(12) United States Patent
Jolliffe et al.

(10) Patent No.: US 7,687,771 B2
(45) Date of Patent: Mar. 30, 2010

(54) HIGH SENSITIVITY MASS SPECTROMETER INTERFACE FOR MULTIPLE ION SOURCES

(75) Inventors: Charles Jolliffe, Schomberg (CA); Gholamreza Javahery, Kettleby (CA); Lisa Cousins, Woodbridge (CA); Ilia Tomski, Concord (CA)

(73) Assignee: Ionics Mass Spectrometry Group, Concord, ON (CA)

( * ) Notice: Subject to any disclaimer, the term of this patent is extended or adjusted under 35 U.S.C. 154(b) by 272 days.

(21) Appl. No.: 11/652,649

(22) Filed: Jan. 12, 2007

(65) Prior Publication Data

US 2007/0181800 A1     Aug. 9, 2007

Related U.S. Application Data

(60) Provisional application No. 60/758,202, filed on Jan. 12, 2006.

(51) Int. Cl.
*H01J 49/04* (2006.01)
*H01J 49/22* (2006.01)

(52) U.S. Cl. .................. 250/285; 250/281; 250/282; 250/288

(58) Field of Classification Search .......... 250/281, 250/282, 285, 288; 702/23, 24, 25, 26, 27, 702/28
See application file for complete search history.

(56) References Cited

U.S. PATENT DOCUMENTS

| | | | |
|---|---|---|---|
| 4,023,398 A | 5/1977 | French | |
| 4,531,056 A | 7/1985 | Labowsky | |
| 4,842,701 A | 6/1989 | Smith | |
| 4,885,076 A | 12/1989 | Smith | |
| 6,501,073 B1 | 12/2002 | Mylchreest et al. | |
| 6,744,041 B2 * | 6/2004 | Sheehan et al. | 250/283 |
| 6,784,422 B2 | 8/2004 | Covey | |
| 6,914,240 B2 | 7/2005 | Giles et al. | |
| 6,956,205 B2 * | 10/2005 | Park | 250/288 |
| 6,979,816 B2 | 12/2005 | Tang et al. | |
| 2004/0079881 A1 * | 4/2004 | Fischer et al. | 250/288 |
| 2005/0194527 A1 * | 9/2005 | Guevremont et al. | 250/285 |

(Continued)

FOREIGN PATENT DOCUMENTS

WO     WO 99/13492     3/1999

*Primary Examiner*—Jack I Berman
*Assistant Examiner*—Nicole Ippolito Rausch
(74) *Attorney, Agent, or Firm*—Hill & Schumacher; Lynn C. Schumacher

(57) ABSTRACT

An interface for mass spectrometers. The interface uses non coaxial sampling pathways of the analyte ion beam prior to entering the entrance of a mass spectrometer for decreasing chemical background, and can be done in such a way as to permit multiple sprayers, increasing sample throughput and sensitivity for LC/MS (liquid chromatography/MS). The interface includes an ion source having an exit from which a beam of analyte ions are emitted, a curtain plate and an aperture in the curtain plate member, an orifice plate having an orifice therein. The orifice plate is being spaced from the curtain plate member defining a flow passageway therebetween, and the aperture in the orifice plate is aligned with a sample entrance to a first vacuum stage of a mass spectrometer maintained substantially lower than atmospheric pressure. The aperture in the curtain plate member is non coaxially aligned with the orifice in the orifice plate and the interface includes a gas flow mechanism for directing a counter flow gas into the flow passageway.

37 Claims, 9 Drawing Sheets

U.S. PATENT DOCUMENTS

2006/0192101 A1* 8/2006 Takada et al. ............... 250/282
2006/0226354 A1* 10/2006 Schneider et al. ........... 250/288
2008/0272285 A1* 11/2008 Giannantonio et al. ...... 250/281
2009/0189064 A1* 7/2009 Miller et al. ................ 250/282

* cited by examiner ized between $10^{-4}$ to $10^{-10}$ torr depending on the mass analyzer type. Thus once created, the charged particles must
HIGH SENSITIVITY MASS SPECTROMETER INTERFACE FOR MULTIPLE ION SOURCES

CROSS REFERENCE TO RELATED U.S. PATENT APPLICATION

This patent application relates to U.S. utility patent application Ser. No. 60/758,202 filed on Jan. 12, 2006 entitled HIGH SENSITIVITY MASS SPECTROMETER INTERFACE FOR MULTIPLE ION SOURCES, filed in English, which is incorporated herein in its entirety by reference.

FIELD OF THE INVENTION

The present invention relates to a method and apparatus for increasing throughput while minimizing intersource interference, increasing sensitivity and reducing chemical noise at the input to a mass spectrometer.

BACKGROUND OF THE INVENTION

Mass spectrometry (MS) is a well-known technique for obtaining a molecular weight and structural information on chemical compounds. According to mass spectrometry, molecules may be "weighed" by ionizing the molecules and measuring the response of their trajectories in a vacuum to electric and magnetic fields. Ions are "weighed" according to their mass-to-charge (m/z) values.

Atmospheric pressure ion sources (API) have become increasingly important as a means for generating ions used in mass spectrometers. Some common atmospheric pressure ion sources include Electrospray or nebulization assisted Electrospray (ES), Atmospheric Pressure Chemical Ionization (APCI), and Matrix Assisted Laser Desorption Ionization (MALDI). These ion sources produce charged particles, such as protonated molecular ions or adduct, from analyte species in solution or solid form, in a region which is approximately at atmospheric pressure.

Conventionally a single type source is used one at a time. However, it is sometimes preferable to use multiple ion sources simultaneously, for example to increase the number of samples analyzed per unit time, also know as throughput. Also, some analyte samples respond well to one approach, such as ESI, and others to another approach such as APCI, and it is desirable to provide a simultaneous approach that is optimal for the formation of charged species.

Mass spectrometers generally operate in a vacuum maintained between $10^{-4}$ to $10^{-10}$ torr depending on the mass analyzer type. Thus once created, the charged particles must be transported into vacuum for mass analysis. A portion of the ions created in the API sources are entrained in the bath gas within the API source chamber and are swept into vacuum along with a carrier gas through an orifice into vacuum. One challenging aspect for high sensitivity lies in efficient transportation of the desired charged ions from atmosphere to the vacuum.

The API sources are advantageous because they provide a gentle means for charging molecules without inducing fragmentation. They also provide ease of use because the sample can be introduced at atmosphere.

API sources have a disadvantage of producing high chemical background and relatively low sensitivity. This is believed to be caused by sampling of impurities attached to the analyte ion (for example, cluster molecules, atoms or ions, or other undesired adduct ions), caused by incomplete desolvation during the API process. In this way, along with desolvated ions, many such droplets of varying diameters can enter into the mass spectrometer and consequently produce a large level of chemical noise across the entire mass range. Additionally incompletely vaporized droplets linger near the sampling orifice.

These problems can be most severe for high liquid sample flow rates, that typically range from 0.2 to 2.0 mL/min. Efficient Electrospray Ionization (ESI) at high flow rate requires sufficient heat for desolvation and a method to deter large clusters from entering the vacuum chamber while enhancing the ion capture. High flow rate analyses are important to industries that have large throughput requirements (such as drug development today, and in the future, protein analysis) because such flow rates are presently necessary for the High pressure Liquid Chromotography (HPLC) techniques performed prior to mass spectrometric analyisis. For most modern applications of ESI and APCI, liquid samples are passed through the source at high flow rates.

To reduce the problem of incomplete desolvation, heated gases are commonly employed to vaporize with a flow direction opposite, or counter, to sprayed droplets in order to desolvate ions at atmospheric pressure. Since the heated gases remove much of the solvent vapor from the stream of gas before being drawn into the vacuum chamber, this technique increases the concentration of ions of interest in the vacuum chamber.

For example, U.S. Pat. No. 4,023,398 teaches a technique whereby ions pass through an orifice into a vacuum chamber, while a gas curtain upstream from the orifice reduces transmission of solvent vapor into the vacuum chamber. The gas is heated to hasten evaporation of the solvent from the droplets, thereby producing desolvated ions at substantially atmospheric pressure. U.S. Pat. No. 4,531,056 teaches a similar technique, whereby an inert gas is introduced into the electrospray chamber in a direction opposite to a flow from the capillary. The electrospray chamber remains at or slightly greater than atmospheric pressure. Ions of interest are produced within the electrospray chamber, and the inert gas flow substantially reduces the concentration of solvent vapor that enters the analyzer. U.S. Pat. Nos. 4,842,701 and 4,885,076 disclose a system that combines capillary zone electrophoresis with electrospray for gas analysis of an analyte mixture. Again, the electrospray occurs at atmospheric pressure, and a heated countercurrent gas flow technique is used to desolvate the spray droplets.

While the counter flowing gas concept described above results in reasonable sensitivity, it is typically incorporated using a largely coaxial geometry between the sprayer and the mass spectrometer. This substantially decreases the ruggedness of the interface between the electrospray and the mass spectrometer, since a portion of the spray can still enter the mass spectrometer. It also reduces the sensitivity since the desolvation time spent in the flow is small.

Now, importantly, it is often useful and desirable to operate with multiple ion sources substantially simultaneously, for example using two or more ESI sources, or an APCI and ESI source, while also reducing the chemical noise and maintaining the simplicity of the atmospheric pressure source. This permits higher throughput or sensitivity (improved signal-to-noise) of sample than is possible with a single ion source, as well as other useful functions such as providing the possibility of on-the-fly calibration. Thus signal-to-noise (sensitivity) and functionality are enhanced, Prior art interfaces exist that contain multiple sprayers. However they are complex devices, requiring moving parts such as rotating cylinders and blocking apertures to select the appropriate sprayer, or utilizing multiple apertures to a vacuum system, thereby increasing vacuum load, increasing cost or reducing sensitivity. For example, U.S. Pat. No. 6,784, 422 teaches approaches for multiple sprayers using multiple sampling apertures directed into the low pressure of the mass spectrometer. It also teaches various approaches to blocking these apertures, and switching the ion beams near these apertures. This approach disadvantageously increases vacuum load, increasing cost or reducing sensitivity.

It is therefore desirable to provide an improved mass spectrometer interface for atmospheric pressure ionization sources suitable for multiple sources having improved sensitivity, enhanced stability and ruggedness and more functionality than prior interfaces, with substantially reduced complexity and cost, and reduced or eliminated source-to-source interference.

SUMMARY OF THE INVENTION

In the broadest aspect of the invention there is provided an interface for a mass spectrometer uses non coaxial sampling pathways of the analyte ion beam prior to entering the entrance of a mass spectrometer for decreasing chemical background, and can be done in such a way as to permit multiple sprayers, increasing sample throughput and sensitivity for LC/MS (liquid chromatography/MS).

In one aspect of the invention there is provided a mass spectrometer interface, comprising:

a) at least a first ion source having an exit from which a beam of analyte ions are emitted;

b) a curtain plate member and a first aperture in the curtain plate member;

c) an orifice plate member having an orifice therein, said orifice plate member being spaced from said curtain plate member defining a flow passageway therebetween, the first aperture in the curtain plate member being non coaxially aligned with the orifice in the orifice plate;

d) gas flow mechanism for directing a counter flow gas into said flow passageway;

e) power supply for applying suitable voltages to the ion source, and the curtain plate member for electrostatic lensing of the analyte ions emitted from an ion source toward a sample entrance through the aperture in the curtain plate member; and f) wherein when analyte ions from the at least a first ion source are directed in an initial flow direction towards the first aperture located in the curtain plate member some of these analyte ions are drawn through the first aperture by an electric field between the orifice plate and the curtain plate, and wherein the analyte ions entering through the first aperture in the curtain plate towards the orifice in the orifice plate encounter a counter flow gas in the flow passageway away from the orifice in the orifice plate, and wherein a low pressure maintained in a vicinity of the sample entrance of a first vacuum stage of a mass spectrometer draws analyte ions through the orifice in the orifice plate towards the sample entrance of the mass spectrometer.

The present invention also provides a mass spectrometer interface, comprising:

a) at least a first ion source having an exit from which a beam of analyte ions are emitted;

b) a curtain plate member and a first aperture in the curtain plate member;

c) an orifice plate member having an orifice therein, said orifice plate member being spaced from said curtain plate member defining a flow passageway therebetween, the first aperture in the curtain plate member being non coaxially aligned with the orifice in the orifice plate;

d) gas flow mechanism for directing a counter flow gas into said flow passageway;

e) power supply for applying suitable voltages to the ion source, and the curtain plate member for electrostatic lensing of the analyte ions emitted from an ion source toward a sample entrance through the aperture in the curtain plate member; and f) wherein when analyte ions from the at least a first ion source are directed in an initial flow direction towards the first aperture located in the curtain plate member some of these analyte ions are drawn through the first aperture by an electric field between the orifice plate and the curtain plate, and wherein the analyte ions entering through the first aperture in the curtain plate towards the orifice in the orifice plate encounter a counter flow gas in the flow passageway away from the orifice in the orifice plate, and wherein a low pressure maintained in a vicinity of the sample entrance of a first vacuum stage of the mass spectrometer draws analyte ions through the orifice in the orifice plate towards the sample entrance of the mass spectrometer, wherein said curtain plate member comprises a counter flow cap including a first elongate tube having a tube wall with the first aperture located in the tube wall and least a first open end and wherein said orifice plate comprises a second elongate tube having opposed first and second ends with the first end being open and forming the orifice and the second end terminating at the sample entrance to a first vacuum stage of a mass spectrometer, wherein a portion of the second elongate tube with the first open end is located within the at least a first open end of the first elongate tube, the counter flow cap and the second elongate tube being positioned with respect to a sample entrance of a mass spectrometer so that the second open end of the second elongate tube opens toward the sample entrance, the portion of the second elongate tube inserted into the at least a first open end of the counter flow cap having a smaller diameter than a diameter of the first elongate tube and wherein an annular space between the counter flow cap and the inserted portion of the second elongate tube forms said flow passageway, and and wherein said gas flow mechanism directs the counter flow gas into said flow passageway from the at least a first open end of the first elongate tube.

The present invention also provides a method of injecting at least one analyte ion beam, produced in at least one ion source, into a mass spectrometer, comprising the steps of:

directing at least one beam of analyte ions towards an inlet structure of a mass spectrometer interface having at least two apertures which are non coaxially aligned with the at least one beam of analyte ions having an ion beam path which has at least two changes of direction prior to entering a sample entrance of a mass spectrometer, a first change of direction being at an angle ($\alpha$) in a range from about 30 to 120 degrees and a second change of direction being at an angle ($\beta$) in a range from about 30 to 120 degrees, such that the at least one beam of analyte ions is traveling in a third direction toward the entrance to the mass spectrometer so that impurities attached to analyte ions in said at least one beam of analyte ions are separated from said analyte ions for reducing chemical background in said at least one analyte ion beam entering said inlet of a mass spectrometer.

The present invention also provides a mass spectrometer interface, comprising:

a) a plurality of ion sources each producing a beam of analyte ions;

b) an inlet structure for passing at least one beam of ions from at least one of said plurality of ion sources into a sample entrance of a mass spectrometer;

c) selection mechanism for selecting a pre-selected number of the ion beams for passage through the inlet structure into the sample entrance of the mass spectrometer while blocking any remaining ion beams, said selection mechanism including a plurality of steering gas sources with each of said plurality of steering gas sources being associated with a respective ion source so that gas emitted from a selected steering gas source intersects with the beam of analyte ions emitted by respective ion source associated therewith and directs said beam of analyte ions into said inlet structure, and including a pulse controller for independently pulsing each of said plurality of steering gas sources on and off, depending on which ion beam or ion beams are to be selected.

A further understanding of the functional and advantageous aspects of the invention can be realized by reference to the following detailed description and drawings.

BRIEF DESCRIPTION OF THE DRAWINGS

The method and apparatus for increasing throughput and sensitivity and reducing chemical background in mass spectrometry, in accordance with the present invention will now be described, by way of example only, reference being made to the accompanying drawings, in which.

DETAILED DESCRIPTION OF THE INVENTION

The systems described herein are directed, in general, to embodiments of interfaces for ion sources for mass spectrometers and particularly interfaces for multiple ion sources. Although embodiments of the present invention are disclosed herein, the disclosed embodiments are merely exemplary and it should be understood that the invention relates to many alternative forms, including different shapes and sizes. Furthermore, the Figures are not drawn to scale and some features may be exaggerated or minimized to show details of particular features while related elements may have been eliminated to prevent obscuring novel aspects. Therefore, specific structural and functional details disclosed herein are not to be interpreted as limiting but merely as a basis for the claims and as a representative basis for enabling someone skilled in the art to employ the present invention in a variety of manner. For purposes of instruction and not limitation, the illustrated embodiments are all directed to embodiments of interfaces for ion sources for mass spectrometers.

As used herein, the term "about", when used in conjunction with ranges of dimensions of particles or other physical properties or characteristics, is meant to cover slight variations that may exist in the upper and lower limits of the ranges of dimensions so as to not exclude embodiments where on average most of the dimensions are satisfied but where statistically dimensions may exist outside this region. It is not the intention to exclude embodiments such as these from the present invention.

Figure 1:
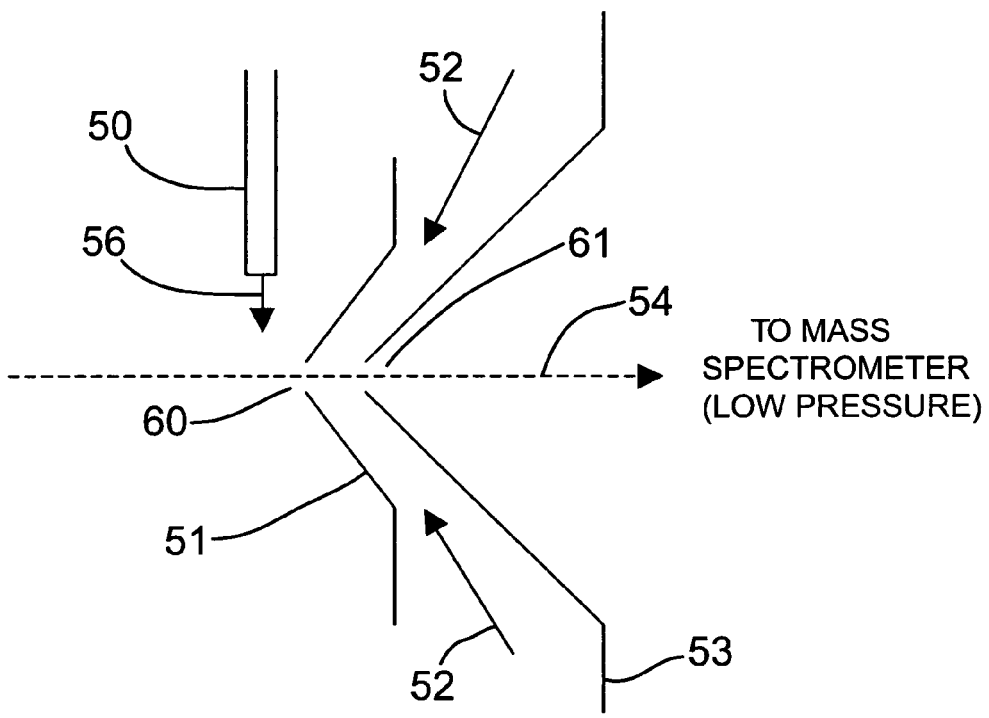
FIG. 1 shows a side view of a Prior Art ion sampling interface for directing an analyte ion beam into a mass spectrometer.

FIG. 1 shows a prior art design of a typical ion sampling arrangement into a mass spectrometer. Ions generated from an atmospheric ion source 50 are sent in the direction 56 towards a mass spectrometer inlet structure which includes the counter plate aperture 60 located in the counter plate 51. These ions are drawn through the aperture 60 located in counter plate 51 through the counter flow gas 52 towards the aperture 61 located in sampling plate 53 which leads into the first stage of the mass spectrometer. Both apertures 60 and 61 are aligned along a common axis 54 so that both apertures 60 and 61 are "coaxially aligned" as the term is used herein. Typical voltages for an electrospray positive ion source 50, the counter plate 51, and the sampling plate 53 are 5000V, 1000V, and 100V, respectively. These voltages ensure the positive ions are directed from the ion source 50 to the sampling plate aperture 61 whereupon the atmosphere gas flow pushes them into the low pressure region of the first stage of a mass spectrometer. For negative ion detection the polarity of these typical voltages are −5,000V, −1000V, and −100V, respectively. This low pressure region of the first stage of the mass spectrometer is usually less than 10 torr. The spacing between the counter plate aperture 60 and the sampling plate aperture 61 is sufficiently small that desolvation is incomplete and chemical noise is high, which reduces the ion flux through the sampling aperture 61. Large droplets from ion source 50 are sampled in a substantially coaxial geometry to the mass spectrometer, and therefore contaminating particles enter the mass spectrometer, decreasing stability, ruggedness and ease of use. The flow direction pattern herein involves one 90 degree bend from the exit of ion source 50 and along axis 54 into the spectrometer.

Figure 2:
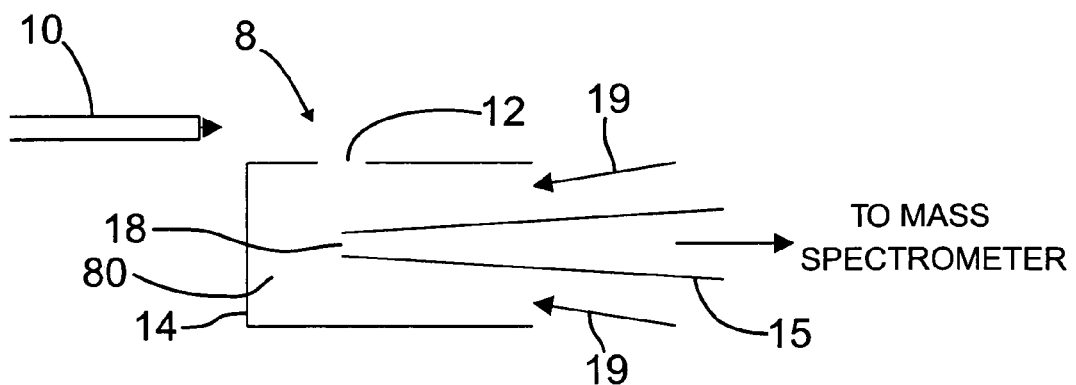
FIG. 2 shows side view of a sample interface for directing an analyte ion beam into a mass spectrometer to enhance sensitivity and ruggedness and reduce chemical noise constructed in accordance with the present invention.

FIG. 2 shows a sample interface for directing an analyte ion beam into a mass spectrometer shown generally at 8 constructed in accordance with the present invention that enhances desolvation, reduces chemical noise and contamination, and permits cost-effective use of multiple sprayers. Ions from atmospheric ion source 10 are directed towards an inlet structure which includes a curtain plate aperture 12 located in a curtain plate member 14 shown in the form of a counter flow cap comprising a first elongate tube. These ions are sampled at roughly 90 degrees to this initial flow direction through aperture 12 located in curtain plate member 14. The counter flow gas 19 is typically clean and dry, and flows in the direction of the region of volume 80 in counter flow cap 14 as shown.

The aperture 12 in the curtain plate member is non coaxial with the orifice or entrance 18 of the orifice plate member 15. Typical sizes of aperture 12 may be in the range of about 1 to about 5 mm. The second elongate tube inserted into the first elongate tube is positioned such that the first opposed end of the second elongate tube is substantially adjacent to the aperture. Typical spacing of aperture 12 and the aperture 18 may be about 3-10 mm Ions from the aperture 12 are directed towards the orifice 18 located in the orifice plate member 15 shown in the form of a second elongate tube. A vacuum pump is located on the first stage of the mass spectrometer and results in a low pressure, typically less than about 10 torr in the elongate tube 15 resulting in the ions being drawn through the orifice 18 in elongate tube 15. The orifice plate 15 when in the form of the tube as shown does not need to have a constant diameter, but can be cone-shaped as shown. Typical diameters of orifice 18 are about 200-1000 micron and the pump speed of the vacuum pump is in the range of about 25-80 l/min. The counter gas flow in direction 19 is maintained to ensure a mild velocity (typically about 0.1-2 m/s) of counter flow gas through counter cap aperture 12 from volume 80. Typical voltages required to produce a positive ion flow from atmospheric ion source 10, counter flow cap 14 and elongate tube 15 may be about 5,000V, 500-2000V, and 0-100V, respectively. The ions from the ion source 10 are drawn into the region 80 within flow cap 14 against the flow 19 of the counter gas through aperture 12 by the potential difference between the inner tube 15 and the counter flow cap 14.

Figure 2A:
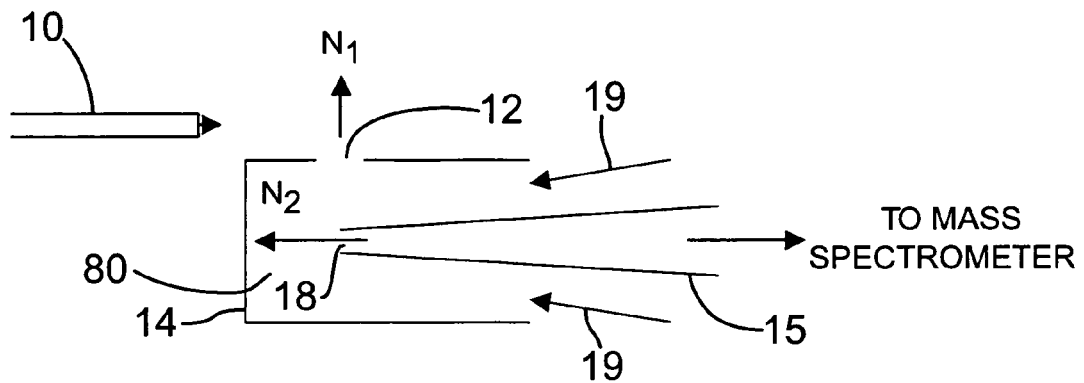
FIG. 2*a* is similar to FIG. 2 but showing the normals to the apertures in the inlet structure.

In general, in the embodiment of the sample interface shown at 8 in FIG. 2 the distance of the counter cap aperture 12 to sampling tube aperture 18 may be more than twice the distance of the counter plate aperture 60 to sampling plate aperture 61 in FIG. 1. For example, aperture 12 may be displaced from aperture 18 by about 5 mm-10 mm. In addition, in FIG. 2, the ion flow direction changes through two 90 degree bends before being admitted into the low pressure region of the mass spectrometer. Referring to FIG. 2a, in the non coaxial arrangement of aperture 12 and orifice 18, the angle between the normal N1 to the first aperture in tube 14 and the normal N2 to the orifice in tube 15 is 90 degrees. With the positioning of the aperture 12 being adjacent to orifice 18 the path followed by the analyte ion beam has two 90 degree bends. The first 90 degree bend prevents a portion of the spray from entering volume 80, but is not sufficient to prevent contamination and all droplets from entering the mass spectrometer. A second bend between aperture 12 and aperture 18 provides further protection from contamination as well as a longer transit path in the counterflow gas. More bends in the ion flow from the ion source 50 would assist in removing large droplets that are incapable of sharp flow direction changes. Although a 90 degree line of site is shown between aperture 12 and aperture 18, other substantially non-coaxial angles such as about 30 degrees, 45 degrees, 120 degrees, or 135 degrees would be suitable, preventing line of site from any portion of the spray (and therefore contamination) from entering the mass spectrometer, while providing a longer transit time and more collisions for effective desolvation. Thus this longer desolvation time very advantageously increases the sensitivity of the mass spectrometer. Both of these bends assist in increasing sensitivity, reducing chemical noise and system contamination. Counter flow gas 19 may be heated to further assist desolvation.

Figure 3:
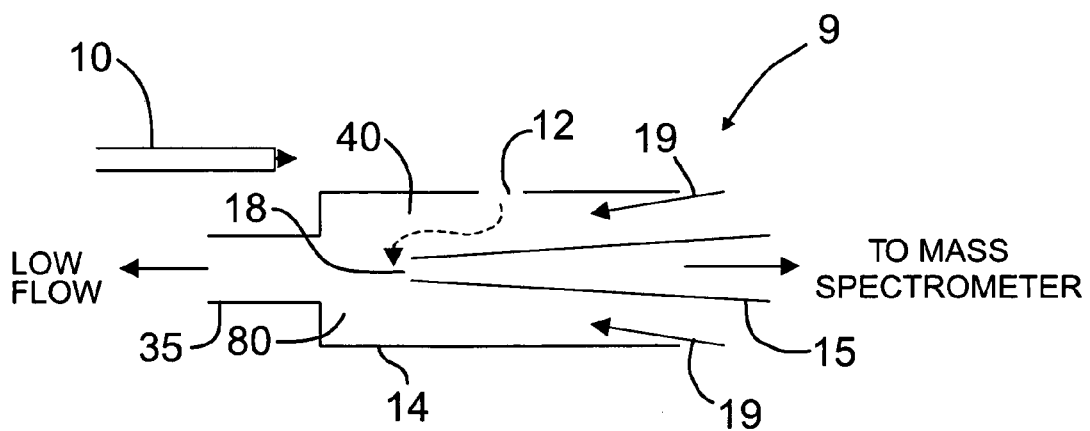
FIG. 3 shows side view of an alternative embodiment of a sample interface.

FIG. 3 shows an alternative embodiment of a portion of a sample interface 9 into the mass spectrometer which is a modification of the sample interface 8 shown in FIG. 2. To further increase the time for ion desolvation, in the embodiment shown at 9 in FIG. 3, the flow cap aperture 12 located in flow cap 14 has been displaced relative to the front open end 18 of the sampling tube 15 by about 3-10 mm. An opening 35, in the front of the counter flow cap 14 is connected to an outlet for the counter flow gas 19. Counter flow gas may now have a larger velocity component within elongate tube of the flow cap 14, for example in the range of about 1 to about 20 m/s, to prevent diffusion losses within the volume, and to direct the analyte ion flow toward the orifice in open end 18 of tube 15. Thus counter flow gas velocity is maintained through the counter cap aperture 12, while analyte ion current drawn through cap aperture 12, and approximately following path 40 (the broken line in FIG. 3) the analyte current is pushed towards the front of the sampling tube 15, and then towards it's opening 18 by the counter flow gas, to be then pushed down the sampling tube 15 by the flow of gas from the predominantly atmospheric pressure cap region downstream to the lower pressure region of the sampling tube 15. In this way, analyte ion current that is comprised of a mixture of completely desolvated ions, partially desolvated ions, and actual charged droplets, is provided more time in which to desolvate, as droplet desolvation at lower pressures is very inefficient, i.e., in the lower pressure regions of the mass spectrometer. Admitting droplets into the mass spectrometer eventually leads to changes in mass spectrometric sensitivity due to surface charge accumulation, and the possibility of chemical noise contamination.

Figure 3A:
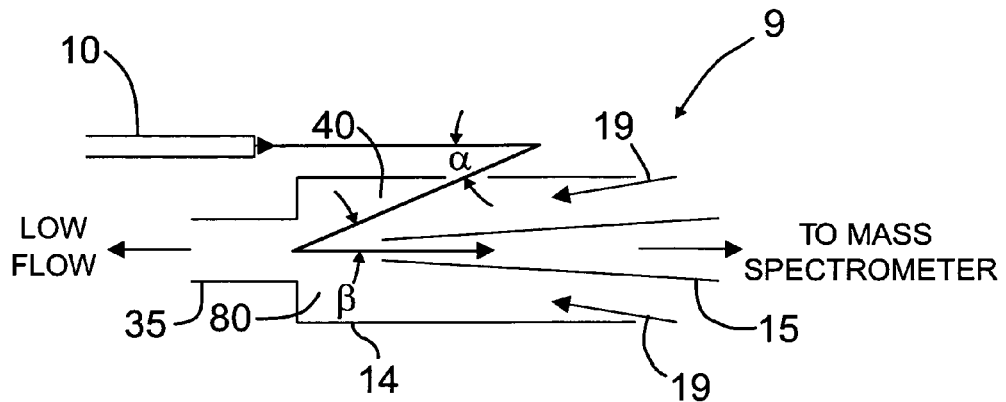
FIG. 3*a* is similar to FIG. 3 but showing the trajectory of a beam of analyte ions through the inlet structure.

Referring to FIG. 3a, in the non coaxial arrangement of aperture 12 and orifice 18, the angle between the normal N1 to the first aperture in tube 14 and the normal N2 to the orifice in tube 15 is still 90 degrees. With the positioning of the aperture 12 being adjacent to orifice 18 the path followed by the analyte ion beam has two 90 degree bends.

While the angle between N1 and N2 in FIGS. 2 and 3 is 90 degrees, it will be appreciated that the present invention is not limited to 90 degrees between the aperture normals but may be any angle as long as they are not coaxially aligned. FIG. 3a shows the trajectory of the analyte ion beam undergoes two changes, the first defined by an angle $\alpha$ and the second defined by an angle $\beta$. The angle $\alpha$ may vary in a range from typically about 30 to 120 degrees and the second angle $\beta$ may vary in a range typically from about 30 to 120 degrees.

Typically, this desolvation process is aided by increasing the temperature of the cap region 80, by directly heating the cap 14, and/or heating the counter flow gas 19. The flow of gas 19 may be assisted by a pump or by a pressurized source.

In order to be able to analyze the output from liquid chromatographs more efficiently using mass spectrometry, it has become important to couple more than one liquid chromatograph to a given mass spectrometer.

Figure 4:
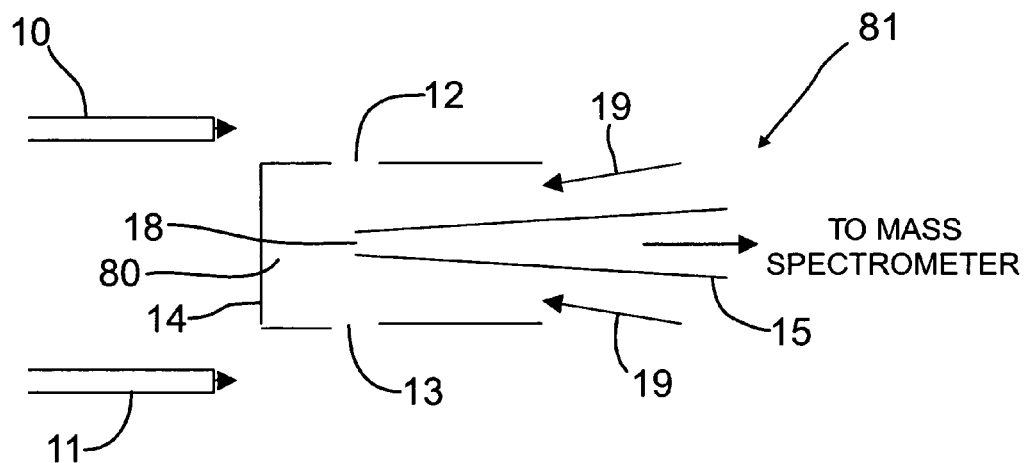
FIG. 4 shows a side view of another alternative embodiment of a sample interface.

FIG. 4 shows another embodiment of a sample interface 81. Sample interface 81 is similar to sample interface 8 in FIG. 2 but includes an additional atmospheric ion source 11 and an additional corresponding counter flow cap aperture 13 located with respect to the end of ion source 11 similar to the location of counter flow cap aperture 12 with respect to the end of atmospheric ion source 10. In this way, the ion outputs of the two separate ion sources 10 and 11 can be combined simultaneously at the sampling tube aperture 18, just before entry into the sampling tube 15, thereby minimizing interaction between the two ion streams from ion sources 10 and 11.

Figure 4B:
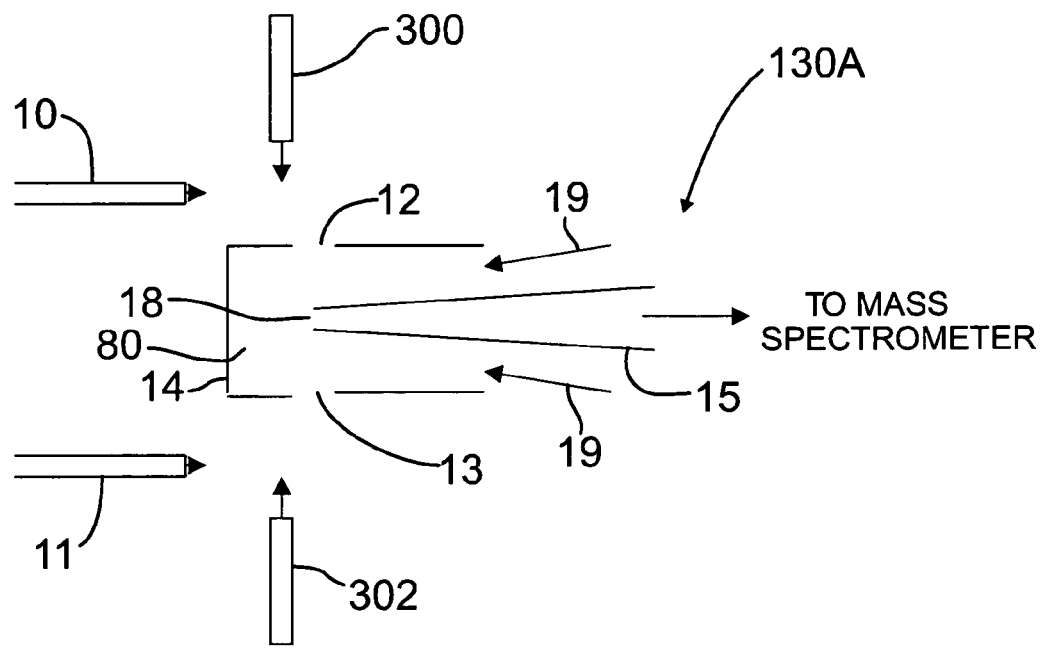
FIG. 4B shows a side view of an alternative embodiment of a sample interface.

In an alternative embodiment of a sample interface into a mass spectrometer shown at 130A in FIG. 4B, the atmospheric ion sources 10 and 11 are displaced relative to the counter flow cap 14, and steering gas sources 300 and 302 are positioned to intersect with the ion sources respectively. Without flow of gas from gas sources 300 and 302, the displacement of atmospheric sources 10 and 11 causes minimal ion flow through apertures 12 and 13, respectively. Although lateral displacement relative to the counter flow cap is shown, angular displacement is also possible. For example, gas source 300 emits gas in the direction shown to steer the ion flow from ion source 10 towards the vicinity of counter flow aperture 12. In a typical application, the steering gas flows 300 and 302 may be pulsed successively to alternately sample ions from ion sources 10 and 11, respectively. An output signal may simultaneously be sent to a recording device to indicate and record which flow 300 or 302 is pulsed on or off. This in turn indicates which ion source is sampled or not sampled. It is preferred to have a gas controlling element (not shown), such as a solenoid valve, positioned reasonably close to the opening so that the gas flow can be controlled quickly. For example, reasonably inexpensive digital solenoid valves from Parker Hannifin Corporation have cycle response times less than 30 msec and life cycle ratings greater than 200 million. Digital gas flow controllers can also be used to provide adjustable flow rates so that ion detection may be optimized. In this embodiment, gas flow from the steering gas sources 300 and 302 are used to observe ions from the ion sources 10, and 11.

Figure 4C:
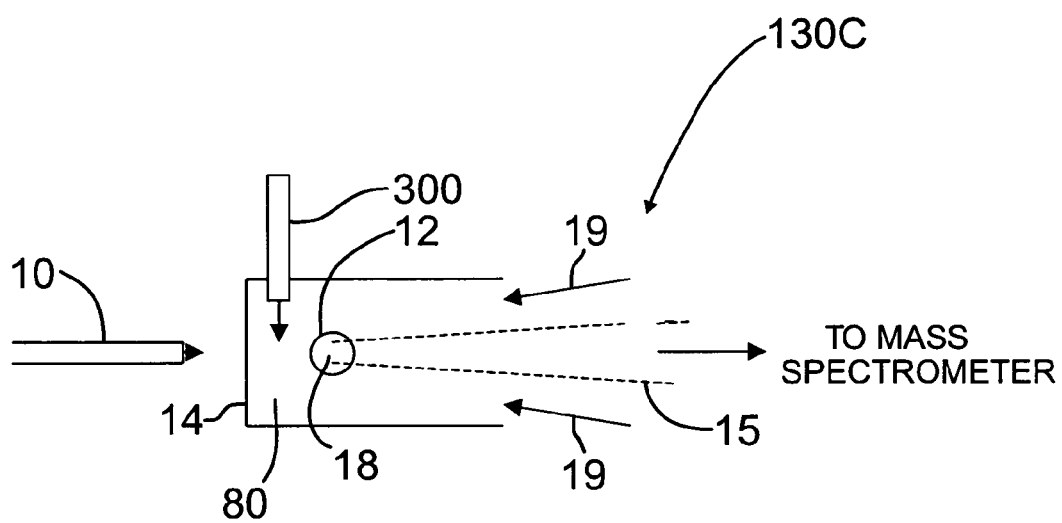
FIG. 4*c* shows a top view of an alternative embodiment of a sample interface.

In another embodiment of a sample interface into a mass spectrometer, a top view of FIG. 4b is shown at 130C in FIG. 4C, and steering gas source 300 is repositioned relative to ion source 10. Ion source 11 is not shown for clarity purposes. In this configuration, gas from steering gas source 300 pushes ions from source 10 away from curtain cap aperture 12 resulting in minimal detection of ions from ion source 10. In this way, ion detection optimization from ion source 10, e.g., the position of ion source relative to aperture 12 and the inherent nebulizing gas flow within ion source 10, can be performed with the gas flow from gas source 300 turned off. In this respect of ease of optimization, embodiment 130C of FIG. 4C is preferred to embodiment 130A of FIG. 4B. Typically the gas flow from gas source 300 will be pulsed off or on as ions from source 10 are to be detected or not, respectively. Similarly, steering gas source 302 (not shown) can be positioned to push ions from ion source 11 away from curtain cap aperture 13 (not shown). As above, an output signal may simultaneously be sent to a recording device to indicate and record which flow 300 or 302 is activated to in turn indicate which ion source (or analyte ion beam) is sampled. In either embodiment 130A or 130C, steering gas flows 300 and 302 may also be heated.

The steering gas sources provide a selection mechanism for selecting a pre-selected number of the ion beams for passage through the inlet structure formed by the curtain cap 14 and the tube 15 into the sample entrance of the mass spectrometer while blocking any remaining ion beams. The selection mechanism may include a plurality of steering gas sources with each of the plurality of steering gas sources being associated with a respective ion source so that gas emitted from a selected steering gas source intersects with the beam of analyte ions emitted by respective ion source associated therewith and directs the beam of analyte ions into said inlet structure. A pulse controller may be used for independently pulsing each of the plurality of steering gas sources on and off, depending on which ion beam or ion beams are to be selected.

While the selection mechanism is shown with the non-coaxially aligned apertures in the inlet structure of FIG. 2 and the various other embodiments described above, it will be appreciated that this selection mechanism may be used or retrofitted into existing inlet structures such as shown in FIG. 1 which use coaxially aligned apertures. Thus, it will be appreciated that the use of a steering gas to steer an ion beam is suitable for any form of ion source or mass spectrometer interface, whether the apertures in the counterflow and sampling regions are coaxial or non coaxial, and as well in the absence of a counterflow gas all together, and therefore as such is not limited to the embodiments in this description Additionally, the pulsing of the steering gas is suitable for any number of embodiments using any number or types of ion sources, not limited to the embodiments within this description.

Figure 5:
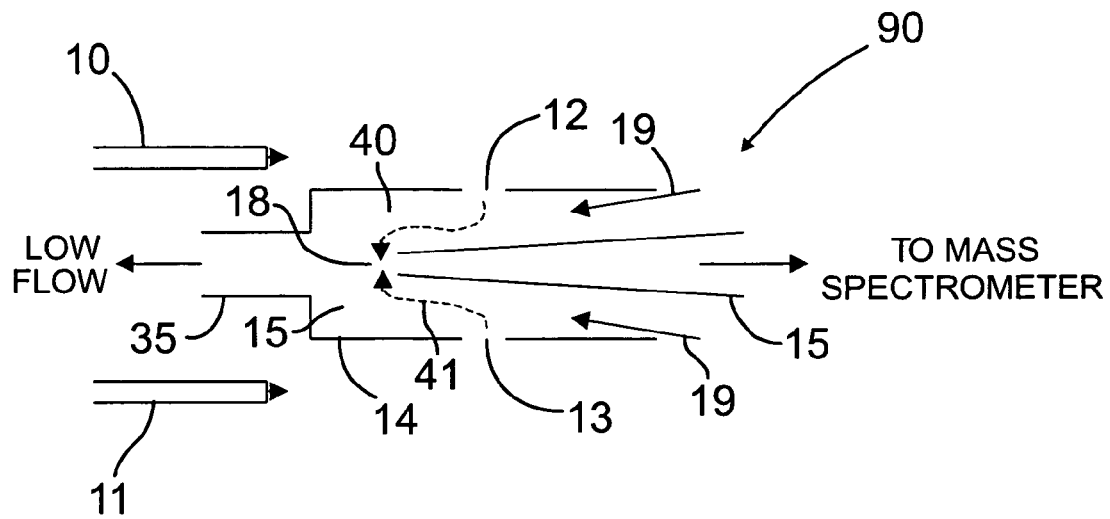
FIG. 5 shows a side view of another alternative embodiment of a sample interface.

In order to increase ion desolvation time in the sample interface 81 into the mass spectrometer in FIG. 4, the counter flow apertures 12 and 13 may be displaced downstream from the exits of the ion sources 10 and 11 in flow cap 24 as shown in the sample interface 90 in FIG. 5, similar to the displacement in FIG. 3. By displacing apertures 12 and 13 in flow cap 14 downstream relative to the sampling tube aperture 18 also effectively displaces them upstream with respect to the counter gas flow 19. As in sample interface 9 shown in FIG. 3, an opening 35 is located in the front of the counter flow cap 14 and is connected to an outlet for the counter flow gas 19.

Alternatively the position of aperture 18 of sampling tube 15 may be displaced relative to the apertures 12 and 13 by a similar amount as in 9 or 90 but with a reverse direction of the curtain gas flow. Further lens may be added to aid in the ion extraction.

Figure 6:
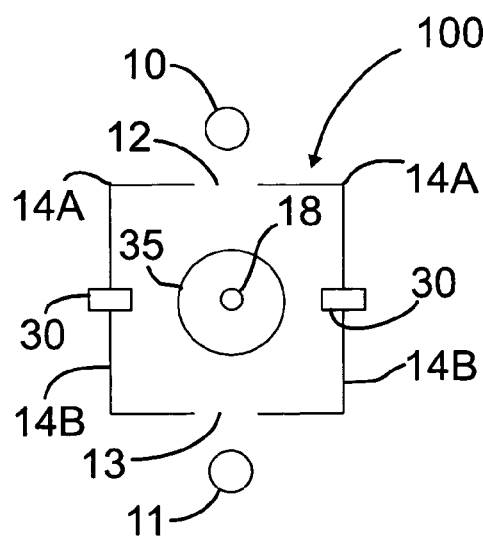
FIG. 6 shows an end view of another alternative embodiment of a sample interface.

FIG. 6 shows another embodiment of a sample interface into a mass spectrometer configured to allow one to sample reactions between opposite polarity ions which is suitable for any embodiment of this invention. In sample interface 100 the counter flow cap 14 is shown as having a square cross-section, for example, and has been separated electrically into two halves, 14A and 14B, with insulators 30. For example, ion source 10 could be an electrospray source producing positive ions and be at 5,000V, with counter flow cap 14A at about 1500V, and the sampling tube 15 at about 0V. At the same time, ion source 11 could be an atmospheric pressure chemical ionization source which includes a corona needle at −6,000V, counter flow cap 14B at −1,500V. In this way, opposite polarity ions react for a short time at atmospheric pressure before being extracted down the sampling tube into a mass spectrometer, or any other detection device.

Figure 7:
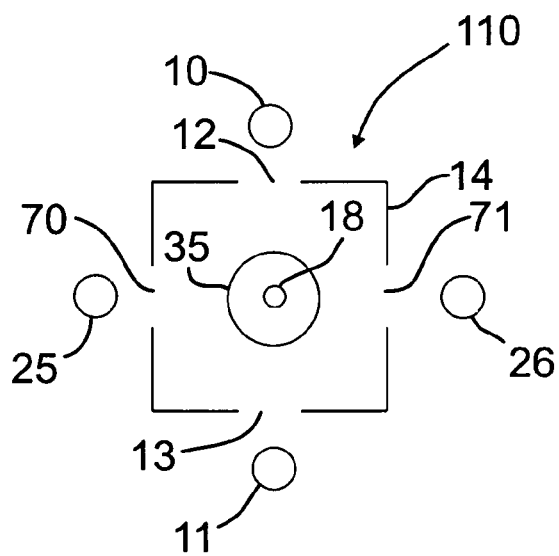
FIG. 7 shows an end view of another alternative embodiment of a sample interface.

The approaches for the interfaces in the embodiments need not be limited to one or two ion sources, as FIG. 7 shows an end view of another embodiment of a sample interface 110 into a mass spectrometer, wherein two additional ion sources 25 and 26, and their corresponding counter flow cap apertures, 70 and 71 are included.

In the different embodiments of sample interfaces into mass spectrometers described above, the ions from the single or multiple ion sources 10, 11, 25 and 26 are introduced simultaneously into the mass spectrometer through the aperture 18 and flow down the sample tube 15.

In sample interface 110 shown in FIG. 7, ions from one or more ion sources can be admitted into to the sampling tube aperture 18, by effectively turning off the ion current from all other ion sources except the ion source, or sources, of interest. Typically, this would involve turning the ion source voltage to that approximately applied to the counter flow cap 14. For example, to admit only positive ions from ion source 25, ion source 25 may be set to approximately 5,000V, ion sources 10, 26, and 11 would set to the counter flow voltage of about 1,000V, and the sampling tube 15 would be set at 0V. An output signal may simultaneously be sent to a recording device to record whether one or more ion source 10, 11, 25 or 26 is sampled.

Another useful feature of multiple sprayers is the ability to provide to one or more sprayers calibration samples or external samples, for example in order to calibrate on the fly or to use an external standard, as may be useful to compensate for instrument drift and improve the accuracy and precision of sample analysis.

Figure 8:
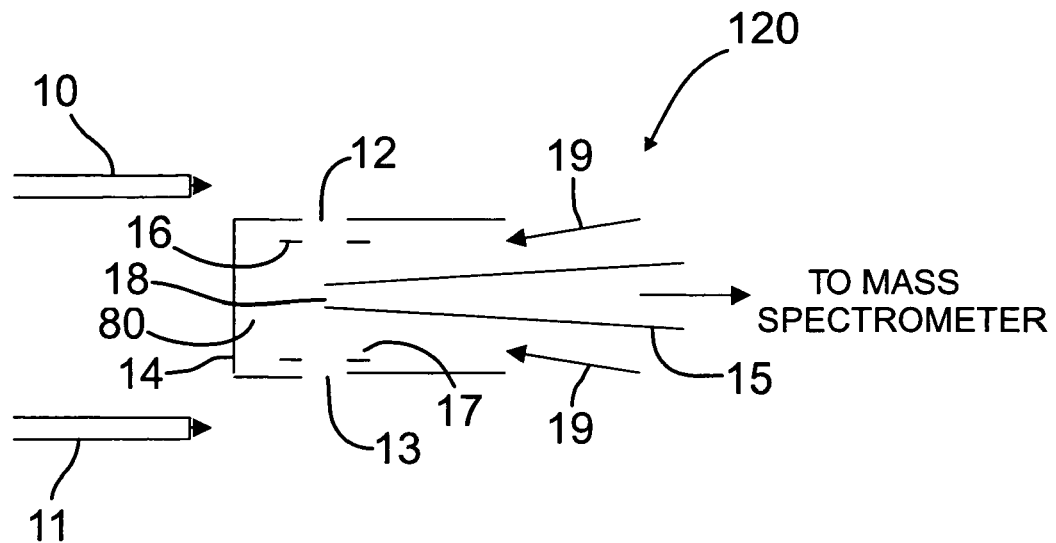
FIG. 8 shows a side view of another alternative embodiment of a sample interface.

Another embodiment of a sample interface into a mass spectrometer shown at 120 in FIG. 8, configured to optionally allow any combination of beams from the different ion sources by addition of lens elements 16 and 17 located just inside flow cap 14 adjacent to apertures 12 and 13 respectively. In this configuration it is possible to switch from one liquid chromatograph output to another by changing the voltages on added lens elements. An output signal may simultaneously be sent to a recording device to record the voltage on lense 16 or 17 to indicate which ion source is sampled. In sample interface 120 the two atmospheric pressure ion sources 10 and 11 may be any one of an electrospray, atmospheric pressure chemical ionization, or atmospheric pressure photoionization ion sources to give a few non-limiting examples. These sources operate at or around atmospheric pressure. Liquid analyte from two liquid chromatographs (not shown) flows into ion sources 10 and 11. Ions emitted from sources 10 and 11 are shown by arrows on sources 10 and 11 as flowing in the direction of apertures 12 and 13 respectively, on the counter flow cap 14. Ions from sprayer 10 and 11 are admitted into the interior 80 of counter flow cap 14 by voltage on the sampling tube 15. Ions are drawn through the front of the sampling tube 15, by the voltage difference applied between the sampling tube 15 and the lenses 16 and 17, and counter flow cap 14, as well as by the flow of gas from the counter flow cap interior 80 down the sampling tube 15.

Typically there is a counter flow of dry clean counter flow gas 19 with a flow sufficient to match the gas flow into the sampling tube 15, and still provide a small outward flow though the apertures 12 and 13 located in flow cap 14.

Figure 9:
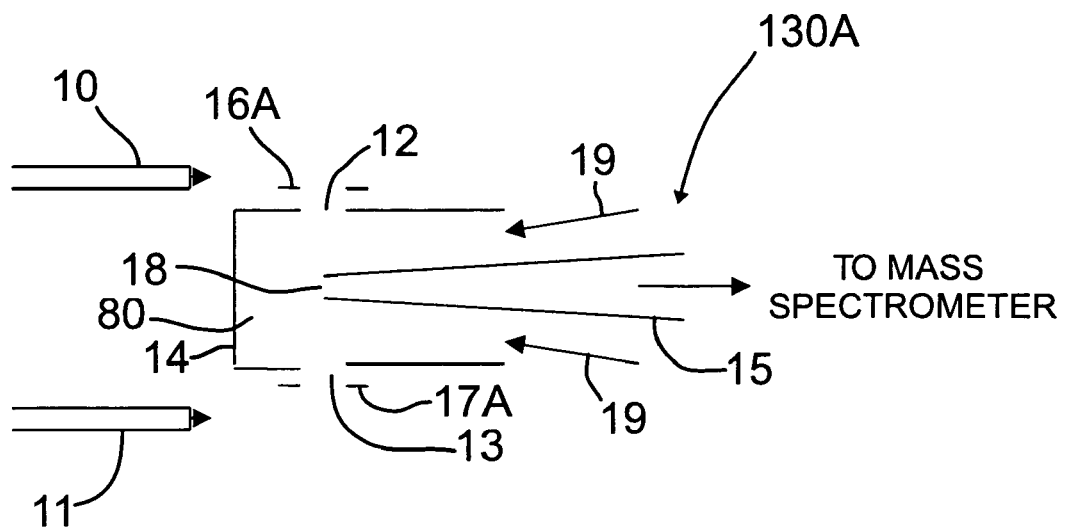
FIG. 9 shows a side view of another alternative embodiment of a sample interface.

In another embodiment of a sample interface into a mass spectrometer shown at 130a in FIG. 9a, the electrostatic lenses 16a and 17a are placed outside the counter flow cap 14 adjacent to their associated apertures 12 and 13 respectively. By appropriate choice of voltages applied to lenses 16a and 17a, the flow of ions may be controlled through apertures 12 and 13 from ion sources 10 and 11.

Figure 10:
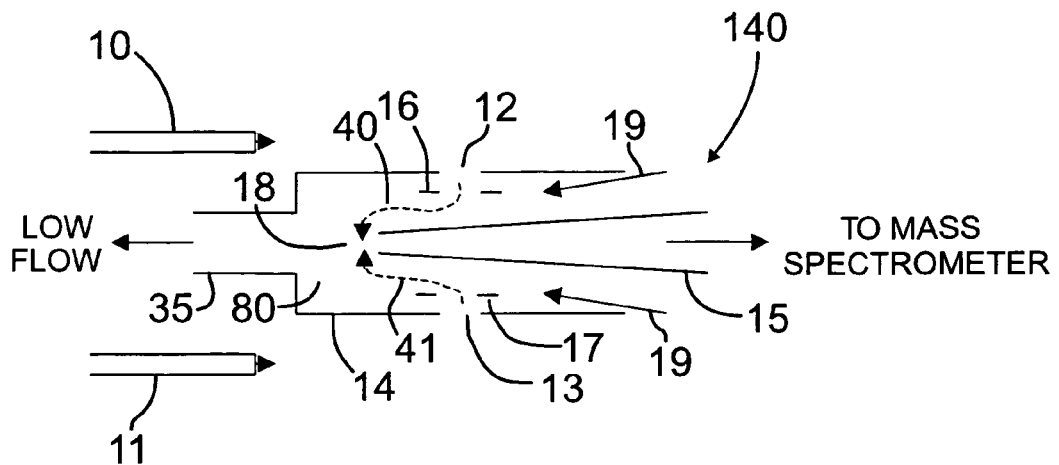
FIG. 10 shows a side view of another alternative embodiment of a sample interface.

In order to further increase the ion desolvation time, sample interface 120 shown in FIG. 8 may be reconfigured to give sample interface 140 shown in FIG. 10. In sample interface 140 the cap apertures 12 and 13 and associated lenses 16 and 17 respectively have been displaced relative to the front aperture 18 of the sampling tube 15. Counter flow gas opening 35 is connected to an outlet for the counter flow gas 19 similar to sample interface 90 in FIG. 5. Analyte current is admitted through cap apertures 12 and 13 by lenses 16 and 17 respectively, approximately along the dotted lines, 40 and 41, respectively, towards the aperture of the sampling tube 18, by the counter flow gas 19, to be then pushed down the sampling tube 15 by the flow of gas from the predominantly atmospheric pressure cap region down to the lower pressure region of the sampling tube. Voltages on lenses 16 and 17 may be switched to select one or more ion sources, with a signal output to record which ion source is sampled.

Figure 11:
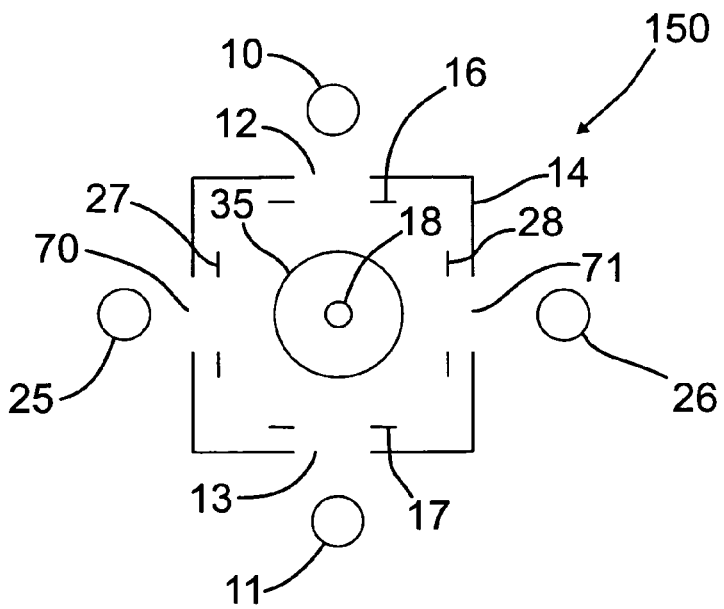
FIG. 11 shows an end view of another alternative embodiment of a sample interface.

FIG. 11 shows an end view of another embodiment of a sample interface 140 configured to double the number of ion sources from the two displayed in FIG. 10. Sample interface 150 includes additional ion sources 25 and 26 spaced downstream from apertures 70 and 71 respectively located in flow cap 14. Lenses 27 and 28 are located inside flow cap adjacent to apertures 70 and 71, respectively. Typical operation involves admitting only one ion source output into the mass spectrometer at a time, with a signal output to record which ion source is sampled. Multiple sprayers may also be admitted simultaneously, with output means to determine which sprayers are sampled.

Figure 12:
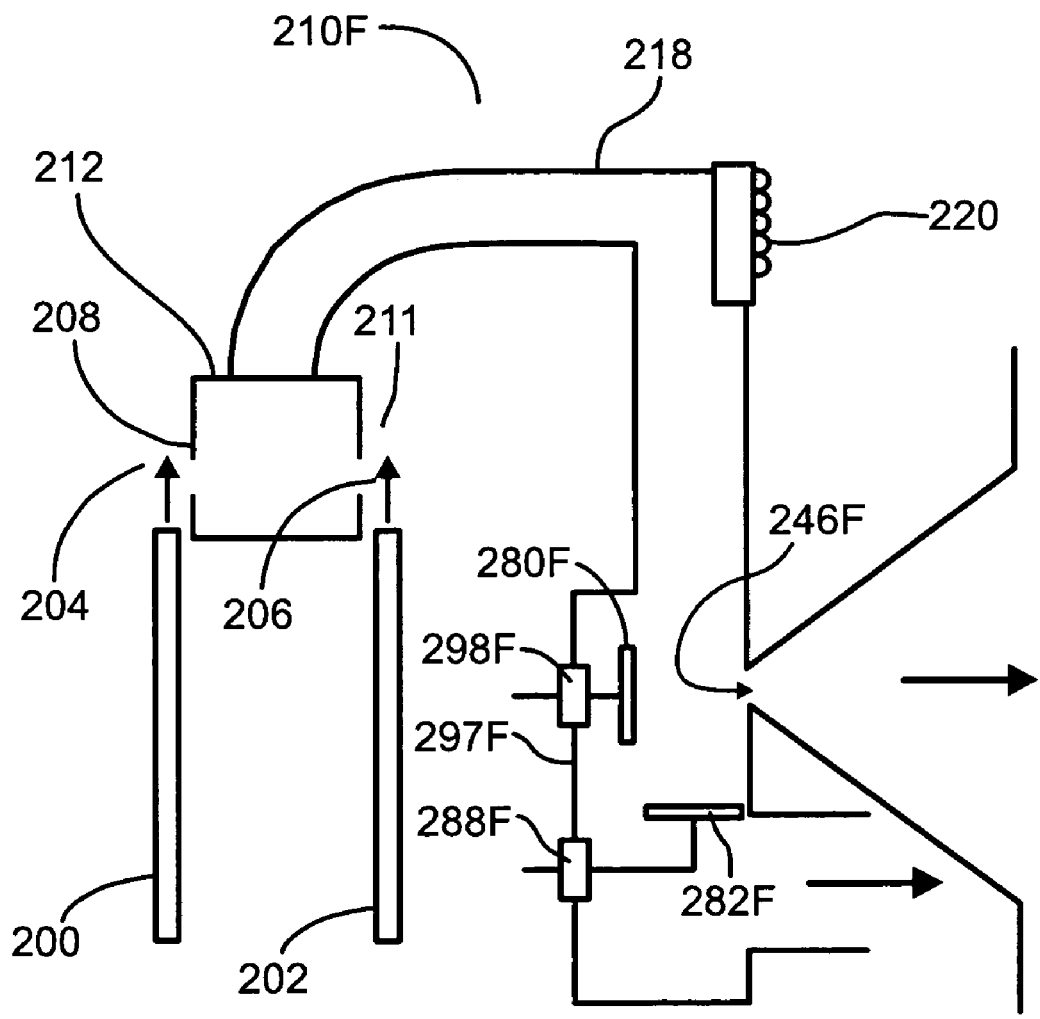
FIG. 12 shows an embodiment of a heated sample interface.

FIG. 12 is an example of another embodiment sampling interface 210F constructed in accordance with the present invention. Two sources 200 and 202 generate ion flows 204 and 206, orthogonally positioned to apertures 208 and 211 in counter flow cap 212. A counter current gas flow (not shown) is passed through 212 to aid in desolvation. The two counterflow cap apertures 208 and 211 are positioned orthogonal to the sampling aperture (not shown). The interface channels 218 and curtain cap 208 may be further heated by means of one or more heaters 220. Ions are entrained in a flow of gas through channel 218, and the channel 218 is pumped by a vacuum pump near 297F. Ions are sampled through aperture 246F into the mass spectrometer. Ion sampling may be aided by deflector devices 280F and 282F, electrically insulated from the housing by insulator supports 288F and 298F.

Figure 13:
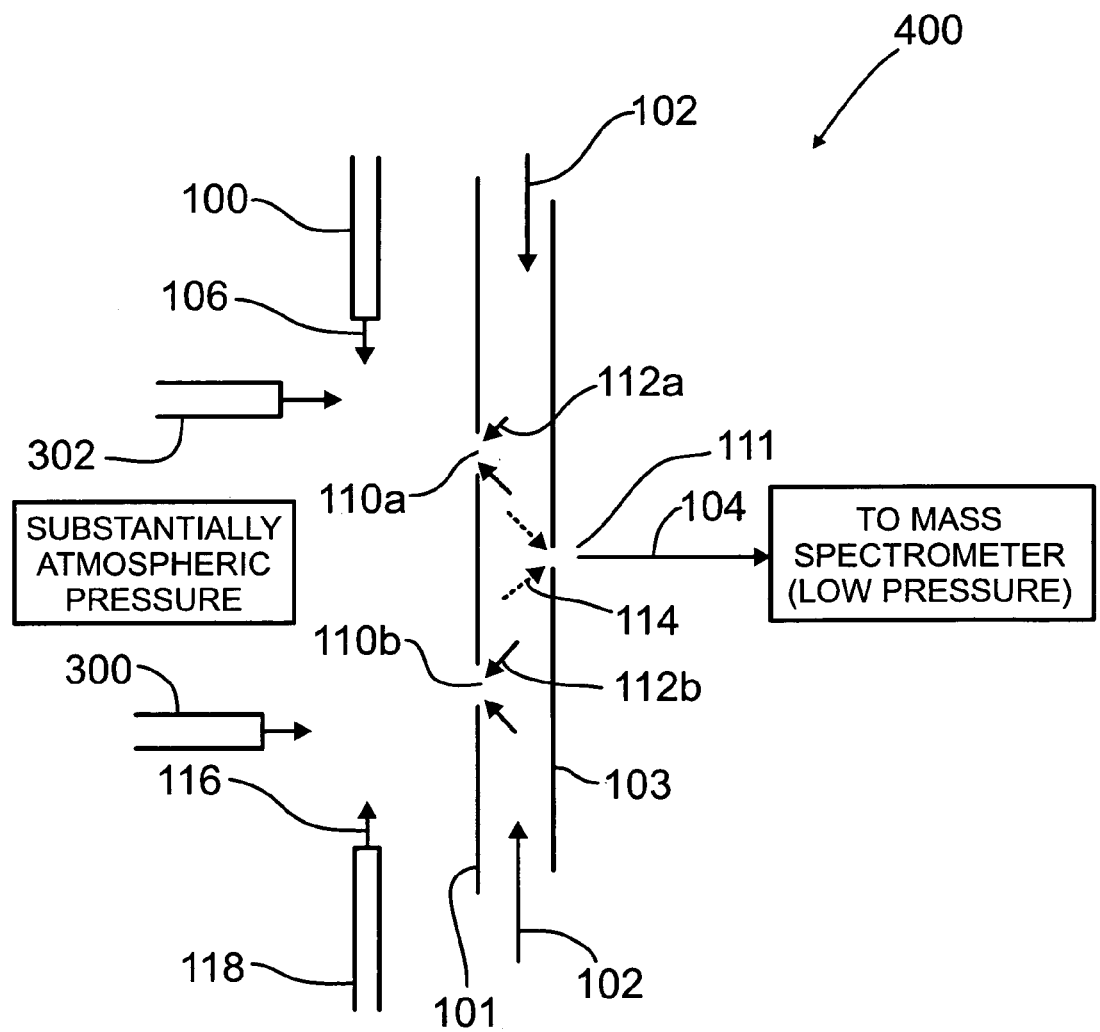
FIG. 13 shows another embodiment an ion sampling interface.

As a further example, FIG. 13 shows an alternative embodiment of a mass spectrometer interface shown generally at 400 for minimizing or reducing multiple sprayer interaction in which the curtain plate member 101 is a plate having two apertures 110a and 110b. The orifice plate member 103 is also a planar plate having an orifice 111 which is aligned with the sample input to the mass spectrometer. Interface 400 uses the same principle of apertures 110a and 110b non-coaxially aligned with orifice 111 as shown in interface 81 shown in FIG. 4 for example. Steering gases 300 and 302 emit gas in the direction shown to steer the ion flow from ion source 118 and 100 towards the vicinity of counter flow apertures 110a and 110b. In a typical application, the steering gas flows 300 and 302 will be pulsed successively to alternately sample ions from ion sources 10 and 11, respectively. Alternatively gas sources 300 and 302 can be configured to selectively steer ions away from apertures 110a and 110b. An output signal indicates which ion source is sampled.

While the counter flow cap 14 shown in the Figures is cylindrical it will be understood that it is not restricted to cylindrical tubes and thus the term "tube" is not to be restricted to cylindrically shaped tubes but tubes of any shape including square, polygonal etc. are to be understood as being covered by the present invention for both the first and second tubes. It is noted that sampling tube 15 is tapered in the Figures but it will be understood that the sampling tube 15 does not need to be tapered and may be straight.

It will be appreciated that all interfaces described above could be configured with steering gas as described in interfaces 130A and 130C of FIGS. 4B and 4C.

It will also be appreciated that in all the embodiments described herein that the operating pressures in the region adjacent to the entrance 18 of sampling tube 15 within the interior of the counter flow cap 14 may be substantially above or below atmosphere, but typically in a range from about 100 Torr to about 2 atmospheres.

It will also be appreciated that in all the embodiments described herein that voltages applied to the ion sources or to electrodes outside of the counterflow region, or to electrodes within the counterflow gas region, may be both DC and time varying, and additional auxiliary gas flows internal and external are within the scope of the invention.

It will also be appreciated that within the embodiments, the multiple ion sources include but are not limited to conventional atmospheric pressure sources such as electrospray ionization, photoionization, and chemical ionization. All interfaces may include an output signal may simultaneously be sent to a recording device to indicate which ion source is sampled. Also, it is sometimes advantageous to have one, two, three or four or more ion sources operating simultaneously, and therefore the descriptions are not limited to operating one ion source at a time.

It will also be appreciated that in all the embodiments described herein that heaters may be placed within or near the counter flow cap 14 or near the ion sources.

As used herein, the terms, "comprises" and "comprising" are to be construed as being inclusive and open ended, and not exclusive. Specifically, when used in this specification including claims, the terms, "comprises" and "comprising" and variations thereof mean the specified features, steps or components are included. These terms are not to be interpreted to exclude the presence of other features, steps or components.

The foregoing description of the preferred embodiments of the invention has been presented to illustrate the principles of the invention and not to limit the invention to the particular embodiment illustrated. It is intended that the scope of the invention be defined by all of the embodiments encompassed within the following claims and their equivalents.

Therefore what is claimed is:

1. A mass spectrometer interface, comprising:
   a) at least a first ion source having an exit from which a beam of analyte ions are emitted;
   b) a curtain plate member and a first aperture in the curtain plate member;
   c) an orifice plate member having an orifice therein, said orifice plate member being spaced from said curtain plate member defining a flow passageway therebetween, the first aperture in the curtain plate member being non coaxially aligned with the orifice in the orifice plate;
   d) gas flow mechanism for directing a counter flow gas into said flow passageway;
   e) power supply for applying suitable voltages to the ion source, and the curtain plate member for electrostatic lensing of the analyte ions emitted from an ion source toward a sample entrance through the aperture in the curtain plate member; and
   f) wherein when analyte ions from the at least a first ion source are directed in an initial flow direction towards the first aperture located in the curtain plate member some of these analyte ions are drawn through the first aperture by an electric field between the orifice plate and the curtain plate, and wherein the analyte ions entering through the first aperture in the curtain plate towards the orifice in the orifice plate encounter a counter flow gas in the flow passageway away from the orifice in the orifice plate, and wherein a low pressure maintained in a vicinity of the sample entrance of a first vacuum stage of a mass spectrometer draws analyte ions through the orifice in the orifice plate towards the sample entrance of the mass spectrometer.

2. The interface according to claim 1 including a pressure controller for maintaining a pressure in a volume defined between said curtain plate member and said orifice plate member of at least about 100 Torr.

3. The interface according to claim 1 including at least one steering gas source positioned so that gas emitted from said at least one steering gas source intersects with the analyte ions emitted by the at least one steering gas source to steer analyte ions with respect to said aperture in the curtain plate member.

4. The interface according to claim 3 including a heater for heating the steering gas.

5. The interface according to claim 1 including a heater for heating the curtain plate member and the orifice plate member to further enhance desolvation.

6. The interface according to claim 1 wherein an angle between the aperture in the curtain plate member and the orifice in the orifice member is between about 30 degrees and about 135 degrees.

7. The interface according to claim 1 wherein an angle between the aperture in the curtain plate member and the orifice in the orifice member is between about 45 degrees and about 135 degrees.

8. The interface according to claim 1 wherein an angle between the aperture in the curtain plate member and the orifice in the orifice member is between about 90 degrees and about 135 degrees.

9. The interface according to claim 1 wherein an angle between the aperture in the curtain plate member and the orifice in the orifice member is between about 100 degrees and about 135 degrees.

10. The interface according to claim 1 wherein said curtain plate member is a first planar metal plate, and wherein said orifice plate member is a second planar metal plate spaced from said first planar metal plate, and wherein the at least a first ion source is positioned with respect to said curtain plate member so that said first aperture is located downstream of said exit.

11. The interface according to claim 1 including a first electrostatic lens electrode located adjacent to said first aperture and wherein said power supply is configured to apply pre-selected voltages to said first electrostatic lens electrode.

12. The interface according to claim 1 wherein said curtain plate member includes a second aperture spaced from said first aperture and in non coaxial relationship with respect to said orifice, including a second ion source having an exit for producing an analyte ion beam and wherein the second ion source is positioned with respect to said curtain plate member so that said second aperture is located downstream of said exit, and wherein said power supply is configured for switching at least voltages on the first and second ion sources on and off, depending on which beam of analyte ions is to be selected.

13. The interface according to claim 12 including two steering gas sources, a first steering gas source being associated with the first ion source and the second being associated with the second ion source, the first steering gas source being positioned so that gas emitted from said first steering gas source intersects with the analyte ions emitted by the first ion source and the second steering gas source being positioned so that gas emitted from said second steering gas source intersects with the analyte ions emitted by the second ion source to steer analyte ions from the two ion sources with respect to said aperture in the curtain plate member, and including a pulse controller for pulsing the first and second steering gas sources on and off, depending on which ion beam is to be selected.

14. The interface according to claim 13 wherein said pulse controller includes a signal means for indicating which of said first and second steering gas sources are switched on or off for recording which steering gas source is switched on or off.

15. The interface according to claim 12 wherein said power supply includes indicator means for indicating which of the first and second ion sources is switched on or off.

16. The interface according to claim 12 including a first electrostatic lens electrode located adjacent to said first aperture, and including a second electrostatic lens electrode located adjacent to said second aperture, and wherein said power supply is configured to independently apply pre-selected voltages to said first and second electrostatic lens electrodes.

17. The interface according to claim 16 wherein said power supply is configured for switching voltages on the first and second lens electrodes on and off, depending on which beam of analyte ions is to be selected.

18. The interface according to claim 17 wherein said power supply includes indicator means for indicating which of the first and second ion sources is switched on or off.

19. The interface according to claim 1 wherein said at least a first ion source is orientated with respect to said first aperture, and said first aperture is non coaxially oriented with respect to said orifice in said orifice plate member such that a path of the at least one beam of analyte ions from said first ion source to the sample entrance of the mass spectrometer has at least two changes of direction, a first change of direction being at an angle ($\alpha$) in a range from about 30 to 120 degrees and a second change of direction being at an angle ($\beta$) in a range from about 30 to 120 degrees.

20. A mass spectrometer interface, comprising:
a) at least a first ion source having an exit from which a beam of analyte ions are emitted;
b) a curtain plate member and a first aperture in the curtain plate member;
c) an orifice plate member having an orifice therein, said orifice plate member being spaced from said curtain plate member defining a flow passageway therebetween, the first aperture in the curtain plate member being non coaxially aligned with the orifice in the orifice plate;
d) gas flow mechanism for directing a counter flow gas into said flow passageway;
e) power supply for applying suitable voltages to the ion source, and the curtain plate member for electrostatic lensing of the analyte ions emitted from an ion source toward a sample entrance through the aperture in the curtain plate member; and
f) wherein when analyte ions from the at least a first ion source are directed in an initial flow direction towards the first aperture located in the curtain plate member some of these analyte ions are drawn through the first aperture by an electric field between the orifice plate and the curtain plate, and wherein the analyte ions entering through the first aperture in the curtain plate towards the orifice in the orifice plate encounter a counter flow gas in the flow passageway away from the orifice in the orifice plate, and wherein a low pressure maintained in a vicinity of the sample entrance of a first vacuum stage of the mass spectrometer draws analyte ions through the orifice in the orifice plate towards the sample entrance of the mass spectrometer,
wherein said curtain plate member comprises a counter flow cap including a first elongate tube having a tube wall with the first aperture located in the tube wall and least a first open end and wherein said orifice plate comprises a second elongate tube having opposed first and second ends with the first end being open and forming the orifice and the second end terminating at the sample entrance to a first vacuum stage of a mass spectrometer,
wherein a portion of the second elongate tube with the first open end is located within the at least a first open end of the first elongate tube, the counter flow cap and the second elongate tube being positioned with respect to a sample entrance of a mass spectrometer so that the second open end of the second elongate tube opens toward the sample entrance, the portion of the second elongate tube inserted into the at least a first open end of the counter flow cap having a smaller diameter than a diameter of the first elongate tube and wherein an annular space between the counter flow cap and the inserted portion of the second elongate tube forms said flow passageway, and
and wherein said gas flow mechanism directs the counter flow gas into said flow passageway from the at least a first open end of the first elongate tube.

21. The interface according to claim 20 including a heater for heating the counter flow cap and the second elongate tube to further enhance desolvation.

22. The interface according to claim 20 wherein said at least a first ion source is orientated 90 with respect to said first aperture, and wherein said first aperture is oriented 90 degrees to said orifice in said elongate tube.

23. The interface according to claim 20 wherein the portion of the second elongate tube located in the first elongate tube is positioned such that the first opposed end of the second elongate tube is substantially adjacent to the aperture with the orifice at an angle of about 90 degrees with respect to the first aperture, and wherein the first elongate tube has a second closed end spaced from the first open end of the second elongate tube.

24. The interface according to claim 20 wherein said first open end of said second elongate tube is located upstream of said first aperture, and wherein said first elongate tube has a second open end spaced from orifice in the second elongate tube.

25. The interface according to claim 23 wherein said first elongate tube has at least a second aperture in the tube wall spaced a same distance from said second closed end of the first elongate tube as the first aperture, and including at least a second ion source, and wherein the portion of the second elongate tube inserted into the first elongate tube is positioned such that the first opposed end of the second elongate tube is substantially adjacent to the at least a second aperture.

26. The interface according to claim 25 wherein said first ion source is an ion source for producing positive ions, and said second ion source is an ion source for producing negative ions, wherein at least some of the opposite polarity ions from the first and second ion sources react before being extracted down the second elongate tube into the entrance of the mass spectrometer.

27. The interface according to claim 25 wherein said first elongate tube has at least a second aperture in the tube wall spaced a same distance from said second closed end of the first elongate tube as the first aperture, and including at least a second ion source, and wherein the portion of the second elongate tube inserted into the first elongate tube is positioned such that the first opposed end of the second elongate tube is located upstream of said at least a second aperture, and wherein said power supply is configured for switching voltages on at least the first and second ion sources, depending on which beam of analyte ions is to be selected.

28. The interface according to claim 27 wherein said first elongate tube has a rectangular cross section made of first and second tube sections separated by an electrical insulator, wherein said first aperture is located in the first tube section and the at least a second aperture is located in the second tube section, and wherein said power supply is configured to independently apply pre-selected voltages to the first and second rectangular sections.

29. The interface according to claim 28 including a first electrostatic lens electrode located adjacent to said first aperture inside said first elongate tube, and including a second electrostatic lens electrode located adjacent to said at least a second aperture inside said first elongate tube, and wherein said power supply is configured to independently apply pre-selected voltages to said first and second electrostatic lens electrodes.

30. The interface according to claim 29 wherein said power supply is configured for switching voltages on the first and second lens electrodes on and off, depending on which beam of analyte ions is to be selected, and wherein the power supply indicator means for indicating which of the first and second ion sources is switched on or off.

31. The interface according to claim 28 including a first electrostatic lens electrode located adjacent to said first aperture outside said first elongate tube, and including a second electrostatic lens electrode located adjacent to said at least a second aperture located outside said first elongate tube, and wherein said power supply is configured to independently apply pre-selected voltages to said first and second electrostatic lens electrodes.

32. The interface according to claim 31 wherein said power supply is configured for switching voltages on the first and second lens electrodes on and off, depending on which beam of analyte ions is to be selected, and wherein the power supply indicator means for indicating which of the first and second ion sources is switched on or off.

33. The interface according to claim 27 wherein said first ion source is an electrospray source with a positive potential bias applied thereto for producing positive ions, and said second ion source is an atmospheric pressure chemical ionization source with a negative potential bias applied thereto for producing negative ions, wherein opposite polarity ions from the first and second ion sources react for a short time at atmospheric pressure before being extracted down the second elongate tube into the entrance of the mass spectrometer.

34. The interface according to claim 27 including a first electrostatic lens electrode located adjacent to said first aperture inside said first elongate tube, and including a second electrostatic lens electrode located adjacent to said at least a second aperture inside said first elongate tube, and wherein said power supply is configured to independently apply pre-selected voltages to said first and second electrostatic lens electrodes.

35. The interface according to claim 34 wherein said power supply is configured for switching voltages on the first and second lens electrodes on and off, depending on which beam of analyte ions is to be selected, and wherein the power supply indicator means for indicating which of the first and second ion sources is switched on or off.

36. The interface according to claim 27 wherein said power supply includes indicator means for indicating which of the first and second ion sources is switched on or off.

37. The interface according to claim 20 wherein said at least a first ion source is orientated with respect to said first aperture, and said first aperture is oriented with respect to said orifice in said second elongate tube such that a path of the at least one beam of analyte ions from said first ion source to the sample entrance of the mass spectrometer has at least two changes of direction, a first change of direction being at an angle ($\alpha$) in a range from about 30 to 120 degrees and a second change of direction being at an angle ($\beta$) in a range from about 30 to 120 degrees.

* * * * *